(12) United States Patent
Liu et al.

(10) Patent No.: US 12,198,337 B2
(45) Date of Patent: Jan. 14, 2025

(54) OUT-OF-DISTRIBUTION DETECTION FOR ARTIFICIAL INTELLIGENCE SYSTEMS FOR PROSTATE CANCER DETECTION

(71) Applicant: SIEMENS HEALTHINEERS AG, Forchheim (DE)

(72) Inventors: Jingya Liu, Harrison, NJ (US); Bin Lou, Princeton, NJ (US); Ali Kamen, Skillman, NJ (US)

(73) Assignee: Siemens Healthineers AG, Forchheim (DE)

( * ) Notice: Subject to any disclaimer, the term of this patent is extended or adjusted under 35 U.S.C. 154(b) by 369 days.

(21) Appl. No.: 17/648,135

(22) Filed: Jan. 17, 2022

(65) Prior Publication Data

US 2023/0230228 A1   Jul. 20, 2023

(51) Int. Cl.
  *G06T 7/00*   (2017.01)
  *G06V 10/40*   (2022.01)
  *G06V 10/74*   (2022.01)
  *G06V 10/82*   (2022.01)
  (Continued)

(52) U.S. Cl.
  CPC .......... *G06T 7/0012* (2013.01); *G06V 10/40* (2022.01); *G06V 10/761* (2022.01); *G06V 10/82* (2022.01); *G16H 30/40* (2018.01); *G16H 50/20* (2018.01); *G06T 2207/20081* (2013.01);
  (Continued)

(58) Field of Classification Search
  CPC .... G06N 20/10; G06N 3/0455; G06N 3/0464; G06N 3/047; G06N 3/0475; G06N 3/084; G06N 3/094; G06N 5/01; G06N 7/01; G06T 2207/20081; G06T 2207/20084; G06T 2207/30081; G06T 2207/30096; G06T 5/00; G06T 7/0012; G06V 10/40; G06V 10/761; G06V 10/774; G06V 10/778; G06V 10/82; G06V 2201/03; G16H 30/40; G16H 50/20; G16H 50/70
  See application file for complete search history.

(56) References Cited

U.S. PATENT DOCUMENTS

2019/0021677 A1*  1/2019  Grbic ................... G06T 7/11
2019/0156477 A1*  5/2019  Perrin ................. G06T 7/0012
2019/0371450 A1* 12/2019  Lou ..................... G16H 50/30
(Continued)

OTHER PUBLICATIONS

Alireza Mehrtash , "Machine Learning for MRI-guided Prostate Cancer Diagnosis and Interventions," Oct. 2020 , Doctoral dissertation, University of British Columbia), pp. 65-86.*
(Continued)

*Primary Examiner* — Omar S Ismail (57) ABSTRACT

Systems and methods for determining whether input medical images are out-of-distribution of training images on which a machine learning based medical imaging analysis network is trained are provided. One or more input medical images of a patient are received. One or more reconstructed images of the one or more input medical images are generated using a machine learning based reconstruction network. It is determined whether the one or more input medical images are out-of-distribution from training images on which a machine learning based medical imaging analysis network is trained based on the one or more input medical images and the one or more reconstructed images. The determination of whether the one or more input medical images are out-of-distribution from the training images is output.

17 Claims, 7 Drawing Sheets

(51) Int. Cl.
*G16H 30/40* (2018.01)
*G16H 50/20* (2018.01)

(52) U.S. Cl.
CPC .............. *G06T 2207/20084* (2013.01); *G06T 2207/30081* (2013.01); *G06T 2207/30096* (2013.01); *G06V 2201/03* (2022.01)

(56) References Cited

U.S. PATENT DOCUMENTS

| | | | | |
|---|---|---|---|---|
| 2020/0069973 | A1* | 3/2020 | Lou | G16H 30/20 |
| 2020/0402236 | A1* | 12/2020 | Courot | G16H 15/00 |
| 2021/0201482 | A1* | 7/2021 | Hattori | G06V 10/764 |
| 2022/0203125 | A1* | 6/2022 | Vojan | A61N 5/1064 |
| 2022/0208366 | A1* | 6/2022 | Vojan | A61N 5/10 |
| 2022/0392065 | A1* | 12/2022 | Min | A61B 6/481 |

OTHER PUBLICATIONS

Davood Karimi, "Accurate and robust deep learning-based segmentation of the prostate clinical target volume in ultrasound images," Jul. 15, 2019, Medical Image Analysis 57 (2019), pp. 187-194.*

Jingya Liu, "Detecting Out-of-Distribution via an Unsupervised Uncertainty Estimation for Prostate Cancer Diagnosis," Jul. 6, 2022-Jul. 8, 2022, Proceedings of The 5th International Conference on Medical Imaging with Deep Learning, PMLR 172:796-807, 2022, pp. 1-8.*

González, Camila, et al. "Distance-based detection of out-of-distribution silent failures for covid-19 lung lesion segmentation." Nov. 2022, Medical image analysis 82 (2022): 102596, pp. 1-10.*

Fahimeh Fooladgar, "Uncertainty-Aware Deep Ensemble Model for Targeted Ultrasound-Guided Prostate Biopsy," Apr. 26, 2022, 2022 IEEE 19th International Symposium on Biomedical Imaging (ISBI), pp. 1-4.*

Abhejit Rajagopal, "Understanding and Visualizing Generalization in UNets," Jul. 9, 2021, Proceedings of Machine Learning Research 143:665{681, 2021, pp. 666-671.*

American Cancer Society, "Cancer Facts & Figures 2021," 2021, 72 pgs.

Winkel et al., "A Novel Deep Learning Based Computer-Aided Diagnosis System Improves the Accuracy and Efficiency of Radiologists in Reading Biparametric Magnetic Resonance Images of the Prostate," 2021, Investigative Radiology, vol. 56, Issue 10, pp. 605-613.

Yan et al., "MRI Manufacturer Shift and Adaptation: Increasing the Generalizability of Deep Learning Segmentation for MR Images Acquired with Different Scanners," 2020, Radiology: Artificial Intelligence, vol. 2, No. 4, 10 pgs.

Bian et al., "Uncertainty-aware domain alignment for anatomical structure segmentation," 2020, Medical Image Analysis, vol. 64, p. 101732.

Golan et al., "Deep Anomaly Detection Using Geometric Transformations," 2018, 32nd Conference on Neural Information Processing Systems, 12 pgs.

Gong et al., "Memorizing Normality to Detect Anomaly: Memory-Augmented Deep Autoencoder for Unsupervised Anomaly Detection," 2019, In Proceedings of the IEEE/CVF International Conference on Computer Vision, pp. 1705-1714.

Fort et al., "Exploring the Limits of Out-of-Distribution Detection," 2021, arXiv preprint arXiv:2106.03004, 21 pgs.

Liu et al., "Simple and Principled Uncertainty Estimation with Deterministic Deep Learning via Distance Awareness," 2020, ICML 2020 Workshop on Uncertainty and Robustness in Deep Learning, 21 pgs.

Zhou et al., "Anomaly Detection with Robust Deep Autoencoders," 2017, Proceedings of the 23rd ACM SIGKDD International Conference on Knowledge Discovery and Data Mining, pp. 665-674.

Wang et al., "ChestX-ray8: Hospital-Scale Chest X-Ray Database and Benchmarks on Weakly-Supervised Classification and Localization of Common Thorax Diseases," 2017, Proceedings of the IEEE Conference on Computer Vision and Pattern Recognition, pp. 2097-2106.

Ouardini et al., "Towards Practical Unsupervised Anomaly Detection on Retinal Images," 2019, in Domain Adaptation and Representation Transfer and Medical Image Learning with Less Labels and Imperfect Data, pp. 225-234.

Shvetsova et al., "Anomaly Detection in Medical Imaging With Deep Perceptual Autoencoders," 2021, in IEEE Access, vol. 9, pp. 118571-118583.

Winkel et al., "Autonomous Detection and Classification of PI-RADS Lesions in an MRI Screening Population Incorporating Multicenter-Labeled Deep Learning and Biparametric Imaging: Proof of Concept," 2020, Diagnostics, vol. 10, Issue 11, p. 951.

Yu et al., "False Positive Reduction Using Multiscale Contextual Features for Prostate Cancer Detection in Multi-Parametric MRI Scans," 2020 IEEE 17th International Symposium on Biomedical Imaging, pp. 1355-1359.

Park et al., "Learning Memory-Guided Normality for Anomaly Detection," 2020, Proceedings of the IEEE/CVF Conference on Computer Vision and Pattern Recognition, pp. 14372-14381.

Oord et al., "Neural Discrete Representation Learning," 2017, 31st Conference on Neural Information Processing Systems, 11 pgs.

Ahmed et al., "Diagnostic accuracy of multi-parametric MRI and TRUS biopsy in prostate cancer (PROMIS): a paired validating confirmatory study," 2017, The Lancet, vol. 389, No. 10071, pp. 815-822.

Lakshminarayanan et al., "Simple and Scalable Predictive Uncertainty Estimation using Deep Ensembles," 2017, Advances in Neural Information Processing Systems 30 (NIPS 2017), 12 pgs.

Litjens et al., "Computer-Aided Detection of Prostate Cancer in MRI," 2014, IEEE Transactions on Medical Imaging, vol. 33, No. 5, pp. 1083-1092.

Razavi et al., "Generating Diverse High-Fidelity Images with VQ-VAE-2," 2019, Advances in neural information processing systems, p. 14866-14876.

Schelb et al., Simulated clinical deployment of fully automatic deep learning for clinical prostate MRI assessment, 2021, European Radiology, vol. 31, pp. 302-313.

Sung et al., "Global Cancer Statistics 2020: GLOBOCAN Estimates of Incidence and Mortality Worldwide for 36 Cancers in 185 Countries," 2021, CA: a cancer journal for clinicians, vol. 71, Issue 3, pp. 209-249.

Zhou et al., "Encoding Structure-Texture Relation with P-Net for Anomaly Detection in Retinal Images," 2020, Computer Vision—ECCV 2020. ECCV 2020. Lecture Notes in Computer Science, vol. 12365, pp. 360-377.

Liu et al., "Detecting Out-of-Distribution via an Unsupervised Uncertainty Estimation for Prostate Cancer Diagnosis," 2021, 5th edition of Medical Imaging with Deep Learning (MIDL 2022), pp. 1-13.

* cited by examiner

OUT-OF-DISTRIBUTION DETECTION FOR ARTIFICIAL INTELLIGENCE SYSTEMS FOR PROSTATE CANCER DETECTION

TECHNICAL FIELD

The present invention relates generally to out-of-distribution detection for artificial intelligence systems, and in particular to out-of-distribution detection for artificial intelligence systems for prostate cancer detection.

BACKGROUND

Prostate cancer is one of the most common types of cancer. Early detection of prostate cancer is crucial for increasing survival rate. Conventionally, prostate cancer is manually detected by radiologists identifying lesions in multi-parametric magnetic resonance imaging (mpMRI) images. However, such manual detection of prostate cancer is a cumbersome and time-consuming task. Recently, artificial intelligence (AI) systems have been proposed for automatic detection of prostate cancer. However, as the performance of such AI systems is dependent on their training data, such AI systems may predict inaccurate results when the input images are out-of-distribution from the training data.

BRIEF SUMMARY OF THE INVENTION

In accordance with one or more embodiments, systems and methods for determining whether input medical images are out-of-distribution of training images on which a machine learning based medical imaging analysis network is trained are provided. One or more input medical images of a patient are received. One or more reconstructed images of the one or more input medical images are generated using a machine learning based reconstruction network. It is determined whether the one or more input medical images are out-of-distribution from training images on which a machine learning based medical imaging analysis network is trained based on the one or more input medical images and the one or more reconstructed images. The determination of whether the one or more input medical images are out-of-distribution from the training images is output.

In one embodiment, the machine learning based reconstruction network and the machine learning based medical imaging analysis network are trained on the same training images. In one embodiment, the machine learning based medical imaging analysis network comprises a lesion detection network trained for detecting prostate cancer lesions in the one or more input medical images.

In one embodiment, it is determined whether the one or more input medical images are out-of-distribution by extracting features from the one or more input medical images and the one or more reconstructed images using the machine learning based medical imaging analysis network and comparing the extracted features from the one or more input medical images and the extracted features from the one or more reconstructed images to determine whether the one or more input medical images are out-of-distribution from the training images. The extracted features may be compared by calculating an uncertainty score based on a distance between the features extracted from the one or more input medical images and the features extracted from the one or more reconstructed images. The uncertainty score may be compared to a threshold.

In one embodiment, a medical imaging analysis task is performed from the one or more input medical images using the machine learning based medical imaging analysis network. Results of the medical imaging analysis task are output.

In one embodiment, the medical imaging analysis task comprises at least one of classification, detection, segmentation, quantification, or clinical decision making.

These and other advantages of the invention will be apparent to those of ordinary skill in the art by reference to the following detailed description and the accompanying drawings.

DETAILED DESCRIPTION

The present invention generally relates to methods and systems for out-of-distribution detection for artificial intelligence (AI) systems for prostate cancer detection. Embodiments of the present invention are described herein to give a visual understanding of such methods and systems. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, is to be understood that embodiments of the present invention may be performed within a computer system using data stored within the computer system.

Embodiments described herein provide for a semantic-aware out-of-distribution detection framework for AI or machine learning systems trained for prostate cancer detection. The out-of-distribution detection framework detects whether input images, which are input into an AI or machine learning based lesion detection network for prostate cancer detection, are out-of-distribution from the training images on which the lesion detection network is trained. Input images are out-of-distribution from the training images when the input images fall outside of the data distribution of the training data. The out-of-distribution detection framework described herein provides for an image reconstruction network in addition to a pretrained (and fixed) lesion detection network. The reconstruction network generates a reconstructed medical image from an input medical image. The lesion detection network is then applied for extracting features from the input medical image and features from the reconstructed medical image and comparing the extracted features to predict an out-of-distribution uncertainty score.

Embodiments described herein provide the following advantages. First, the reconstruction network learns latent representations via an unsupervised learning method on in-distribution training data only, thus avoiding the requirement for out-of-distribution training images. Second, the latent representations are sampled from a discrete latent space in order to lessen the generalization capacity of the autoencoder. Third, out-of-distribution input medical images are identified by comparing the similarity of the input medical images and the reconstructed images in the latent feature space defined by a pre-trained lesion detection model. This design makes the outliers have higher uncertainty with respect to the lesion detection task. Fourth, the performance of the embodiments described herein was evaluated on a large testing dataset. The performance of the pre-trained lesion detection model is significantly improved by excluding cases determined to be out-of-distribution in accordance with embodiments described herein.

Figure 1:
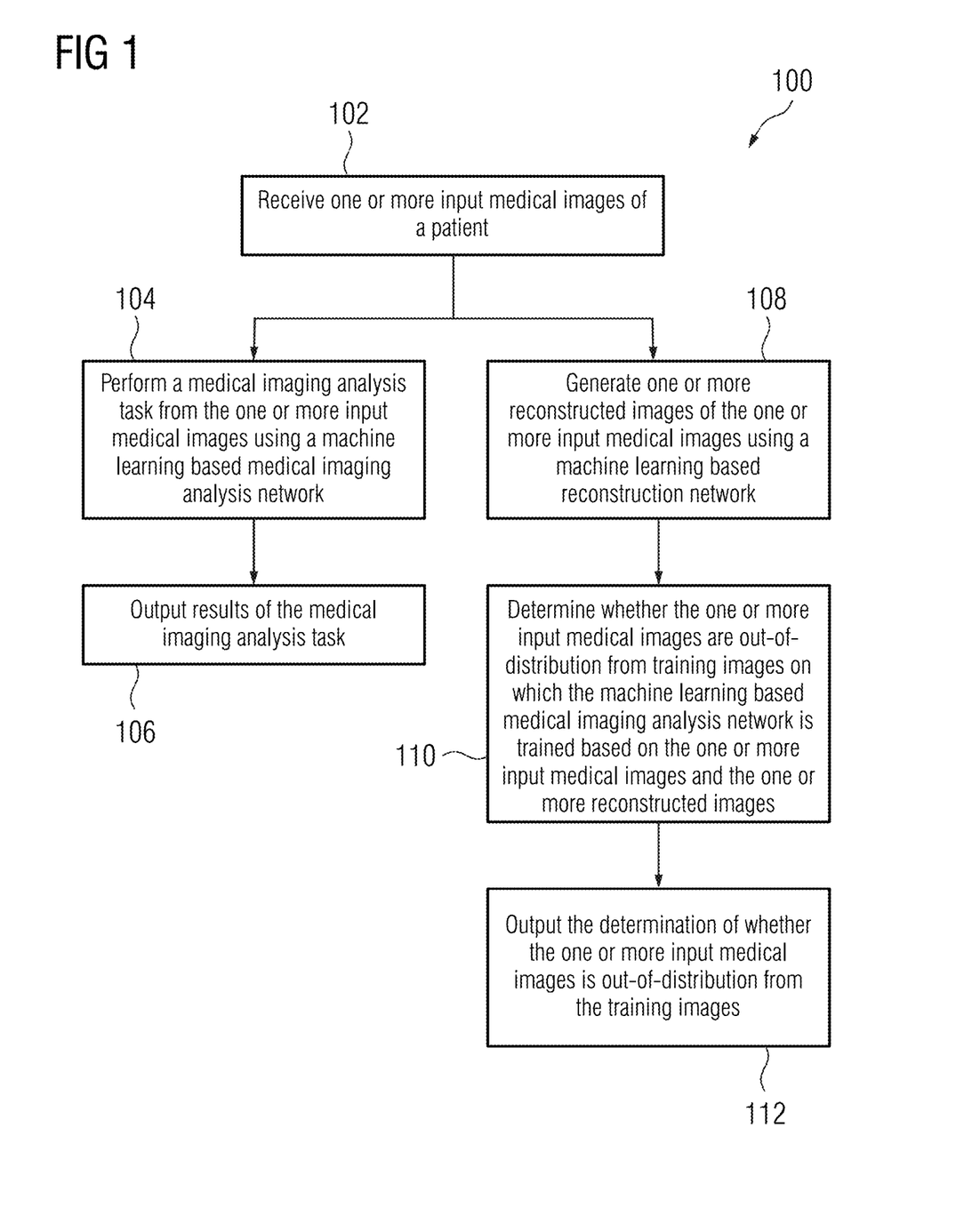
FIG. 1 shows a method for determining whether an input medical image is out-of-distribution from training images on which a lesions detection network is trained, in accordance with one or more embodiments.
Figure 2:
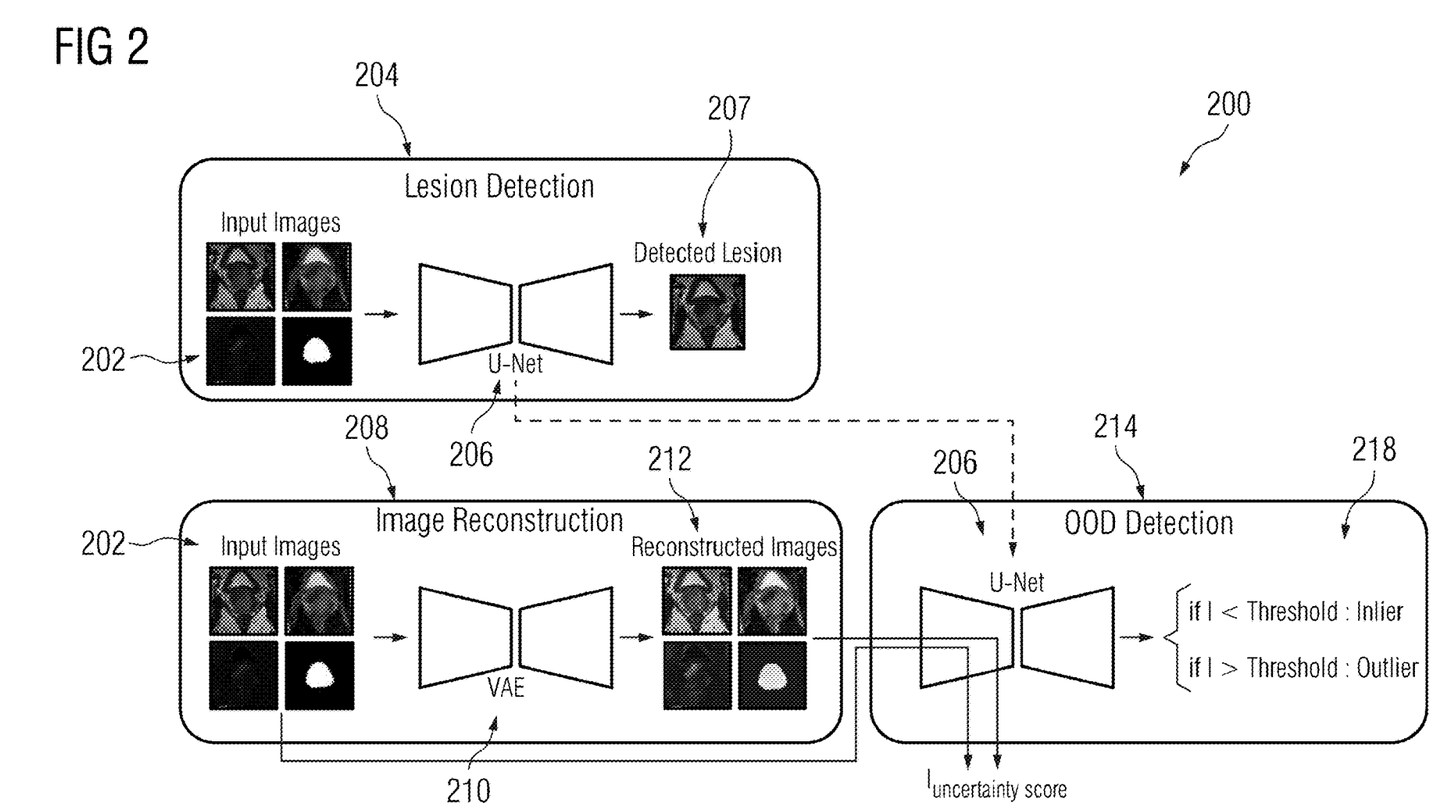
FIG. 2 shows a framework for out-of-distribution detection, in accordance with one or more embodiments.

FIG. 1 shows a method 100 for determining whether an input medical image is out-of-distribution from training images on which a lesions detection network is trained, in accordance with one or more embodiments. The steps of method 100 may be performed by one or more suitable computing devices, such as, e.g., computer 702 of FIG. 7. FIG. 2 shows a framework 200 for out-of-distribution detection, in accordance with one or more embodiments. FIG. 1 and FIG. 2 will be described together.

At step 102 of FIG. 1, one or more input medical images of a patient are received. The one or more input medical images depict an anatomical object of interest, such as, e.g., the prostate. In one example, as shown in FIG. 2, the one or more input medical images are input images 202 of framework 200. While input images 202 are separately shown for lesion detection 204 and image reconstruction 210 in FIG. 2, input images 202 for lesions detection 204 and image reconstruction 208 are the same images.

In one embodiment, the one or more input medical images comprise multiparametric magnetic resonance imaging (mpMRI) images. The mpMRI images may comprise a number of sequences acquired via different imaging protocols. For example, the mpMRI images may comprise a T2-weighted image, an apparent diffusion coefficient (ADC) image, a diffusion-weighted magnetic resonance imaging (DWI) image, and a mask of the anatomical object of interest. However, the one or more input medical images may be of any other suitable modality, such as, e.g., computed tomography (CT), magnetic resonance imaging (MRI), ultrasound (US), x-ray, or any other medical imaging modality or combinations of medical imaging modalities. The one or more input medical images may comprise 2D (two dimensional) images and/or 3D (three dimensional) volumes, and may comprise a single input medical image or a plurality of input medical images.

The one or more input medical images may be received directly from an image acquisition device (e.g., image acquisition device 714 of FIG. 7) as the medical images are acquired, may be received by loading previously acquired medical images from a storage or memory of a computer system (e.g., an EMR (electronic medical record) system or a PACS (picture archiving and communication system)), or may be received by receiving medical images that have been transmitted from a remote computer system.

Method 100 of FIG. 1 may then proceed to step 104 to perform steps 104-106 or to step 108 to perform steps 108-112. Steps 104-106 and steps 108-112 may be performed in any order. For example, steps 104-106 may be performed prior to, simultaneously with, or subsequently to steps 108-112.

At step 104 of FIG. 1, a medical imaging analysis task is performed from the one or more input medical images using a machine learning based medical imaging analysis network. The medical imaging analysis network is pretrained (and fixed) for performing the medical imaging analysis task. In one embodiment, the medical imaging analysis task is lesion detection for detecting lesions (e.g., prostate cancer lesions) in the one or more input medical images using a machine learning based lesion detection network. The lesion detection network may be implemented as a U-Net or any other suitable machine learning based architecture. However, the medical imaging analysis task may be any other suitable medical imaging analysis task, such as, e.g., classification, detection, segmentation, quantification, clinical decision making, etc. using any suitable machine learning based architecture.

In one example, as shown in FIG. 2, the medical imaging analysis task is lesion detection 204 and the medical imaging analysis network is a lesion detection network 206 implemented as a Res U-Net. Lesion detection network 206 comprises an encoder and a decoder. The encoder of lesion detection network 206 receives input images x 202 as input and encodes input images x 202 into latent features. The decoder of lesion detection network 206 decodes the latent features to generate output image 207 identify candidate regions d(x) of detected lesions. In one exemplary implementation, the encoder of lesion detection network 206 comprises five blocks of encoding layers for extracting the latent features from input images x 202 and downsampling the latent features to 2x, 4x, 8x, and 16x respectively. The decoder of lesion detection network 206 comprises 5 blocks of decoding layers for interpreting the latent features for identifying candidate regions d(x) and upsampling the latent features to 2x, 4x, 8x, and 16x respectively to the original image size. All blocks are represented by residual blocks to prevent the vanishing gradient for better semantic segmentation.

At step 106 of FIG. 1, results (e.g., output image 207) of the medical imaging analysis task are output. For example, the results of the medical imaging analysis task can be output by displaying the results of the medical imaging analysis task on a display device of a computer system, storing the results of the medical imaging analysis task on a memory or storage of a computer system, or by transmitting the results of the medical imaging analysis task to a remote computer system.

At step 108 of FIG. 1, one or more reconstructed images of the one or more input medical images are generated using a machine learning based reconstruction network. The one or more reconstructed images are respective reproductions of the one or more input medical images by the reconstruction network. In one embodiment, the reconstruction network is implemented as a variational autoencoder (VAE). However, the reconstruction network may be implemented according to any suitable machine learning based architecture. The reconstruction network and the medical imaging analysis network are trained using the same training data. Notably, the reconstruction network is trained via unsupervised learning, thus avoiding the requirement for annotated out-of-distribution training images.

In one example, as shown in FIG. 2, the generation of the one or more reconstructed images is represented as image reconstruction 208 performed using a reconstruction network 210 implemented as a VAE. Reconstruction network 210 comprises an encoder and a decoder. The encoder of reconstruction network 210 receives input images x 202 as input and encodes input images x 202 into latent features $z_e(x)$. The decoder of reconstruction network 210 decodes the latent features $z_e(x)$ to generate reconstructed images $\hat{x}$ 212. In one embodiment, in order to extract informative features from input images 202, instead of directly generating the reconstructed images from the latent features $z_e(x)$, reconstruction network 210 is implemented as a vector quantized VAE (VQ-VAE) to integrate the latent features $z_e(x)$ from a posterior network with an embedding table, where the common features are embedded in N of K dimensional one-hot vector e. In this embodiment, the nearest embedding $e_i$ in the codebook table from the latent features $z_e(x)$ is found via the L2 distance and the nearest embedding $e_i$ is input into the decoder to generate the reconstructed images. Reconstruction network 210 is trained on unlabelled training images, as discussed in further detail below.

At step 110 of FIG. 1, it is determined whether the one or more input medical images are out-of-distribution from training images on which the machine learning based medical imaging analysis network is trained based on the one or more input medical images and the one or more reconstructed images. In one embodiment, it is determined whether the one or more input medical images are out-of-distribution using the medical imaging analysis network. The determination of whether the one or more input medical images are out-of-distribution may be represented as an uncertainty score or in any other suitable form.

In one example, as shown in FIG. 2, the determination of whether the one or more input medical images are out-of-distribution is represented as out-of-distribution (OOD) detection 214 performed using lesion detection network 206, which was pretrained (and fixed) trained for lesion detection 204. While lesion detection network 206 is separately shown for lesion detection 204 and OOD detection 214, lesion detection network 206 for lesion detection 204 and OOD detection 214 is the same lesion detection network. The encoder of lesion detection network 206 receives input images 202 as input and reconstructed images 212 and respectively encodes input images 202 and reconstructed images 212 into latent features. The encoder of lesion detection network 206 then compares the latent features from input images 202 and the latent features from reconstructed images to determine a dissimilarity (or similarity) between the latent features as an uncertainty score. Compared to image-level reconstruction loss, feature-level dissimilarity utilizes more informative features for out-of-distribution detection.

The out-of-distribution detection framework is trained with a perceptual loss $\mathcal{L}_{percept}$ for each block of lesion detection network 206 by applying the L2 loss. The latent features extracted from input images 202 for the i-th block of the encoder of lesion detection network 206 is denoted $f_i(x)$ and the latent features extracted from reconstructed images 212 for the i-th block of the encoder of lesion detection network 206 is denoted $f_i(\hat{x})$. In one exemplary implementation, the first nine blocks of lesion detection network 206 are applied to extract feature-level similarity, where the total weights of the perceptual loss $\mathcal{L}_{percept}$ for each block are normalized to one. The uncertainty score $1_{uncertainty\ score}$ 216 is calculated as the perceptual loss $\mathcal{L}_{percept}$ to evaluate the case-level uncertainty. A higher uncertainty score $1_{uncertainty\ score}$ 216 indicates a larger distance observed in the latent space between the latent features extracted from input images 202 and the latent features extracted from reconstructed images 212. A lower uncertainty score $1_{uncertainty\ score}$ 216 indicates a smaller distance observed in the latent space between the latent features extracted from input images 202 and the latent features extracted from reconstructed images 212. The uncertainty score $1_{uncertainty\ score}$ 216 may be compared 218 with one or more thresholds. If the uncertainty score $1_{uncertainty\ score}$ 216 satisfies (e.g., is smaller than) a threshold, the input images 202 are more likely to be in-distribution (e.g., inlier data) from the training data. If the uncertainty score $1_{uncertainty\ score}$ 216 does not satisfy (e.g., is not smaller than) the threshold, the input images 202 are more likely to be out-of-distribution (e.g., outlier data) from the training data. The perceptual loss $\mathcal{L}_{percept}$ is further described below with respect to Equation 3.

At step 112 of FIG. 1, the determination of whether the one or more input medical images is out-of-distribution from the training images is output. For example, the determination of whether the one or more input medical images is out-of-distribution from the training images can be output by displaying the determination on a display device of a computer system, storing the determination on a memory or storage of a computer system, or by transmitting the determination to a remote computer system.

The out-of-distribution detection framework is trained during a prior offline or training stage using the same set of in-distribution training data. Reconstruction network 210 is trained using an embedding codebook to extract limited discrete latent features and retain the high quality of reconstructed images. The codebook is applied as a vector quantization of hidden variables of the reconstruction network 210 for the learned common features of the in-distribution data. This codebook is an embedding table comprised of K latent embedding vectors $e_i$ with D dimensions (i takes the value of (1, ..., K)). After passing the image through the encoder, a H×W×D dimensional feature map $z_e(x)$ is obtained, where H×W is the height and weight of the feature map, and the D is the dimensionality of feature map. For the H×W D-dimensional feature maps, the nearest embedding $e_j$ in this codebook table is found via the L2 distance and is applied as the embedding vector to replace the original feature map. Thus, instead of directly reconstructing images from the encoded latent features $z_e(x)$, reconstruction network 210 is trained to retrieve the nearest embedded latent feature vector $e_1$ from the codebook, which is input into the decoder of reconstruction network 210 to generate reconstructed images. If reconstruction network 210 is trained with in-distribution training images, the items in the codebook should capture representations of normal samples. During the training, to update the latent vector codebook, a gradient is computed to minimize the L2 distance between the latent features $z_e(x)$ and its nearest embedded feature vector $e_1$, denoted as compactness loss $\mathcal{L}_{compact}$ in Equation 1.

$$\mathcal{L}_{compact} = \|sg(z_e(x)) - e_1\|_2 \quad \text{(Equation 1)}$$

where sg(*) denotes a stop gradient operation that has zero partial derivatives in the backpropagation, thus only optimizing embeddings in the codebook.

To increase the diversity of embeddings for learning various patterns of normal samples, a separateness loss $\mathcal{L}_{separate}$ is applied, as defined in Equation 2. Separateness loss $\mathcal{L}_{separate}$ keeps the distance between the latent features $z_e(x)$ and its nearest embedded feature vector $e_1$ smaller than the distance between the latent features $z_e(x)$ and its second nearest embedded feature vector $e_2$ within a margin m.

$$\mathcal{L}_{separate}=sg(z_e(x))-e_1\|_2-sg(z_e(x))-e_2\|_2+m \quad \text{(Equation 2)}$$

To evaluate the uncertainty relevant to lesion detection, a perceptual loss $\mathcal{L}_{percpt}$ to optimize high-level structure learning for feature-level representations of the in-distribution data for the pretrained lesion detection network 206. A previously validated lesion detection model may be selected to compare the feature differences between input images and reconstructed images. Lesion detection network 206 comprises multiple convolutional layers capable of extracting information at different scales. Since the extracted latent features may comprise important semantic and contextual information for lesion detection, measuring dissimilarities in this feature space is more accurate than in the original image space. The outliers identified in the feature space are more relevant to the specific task (e.g., lesion detection) than general out-of-distribution samples. This design addresses the problem of lacking ground truth labels of out-of-distribution training images by associating the out-of-distribution detection with the specific lesion detection task. Denoting latent features extracted from input medical images for the i-th block of the encoder of lesion detection network 206 as $f_i(x)$ and the latent features extracted from reconstructed images for the i-th block of the encoder of lesion detection network 206 as $f_i(\check{x})$, the perceptual loss $\mathcal{L}_{percpt}$ is computed as the sum of L2 distances between feature maps within the prostate region of all residual blocks:

$$\mathcal{L}_{percpt} = \sum_i \|f_i(x) \odot M(x) - f_i(\check{x}) \odot M(x)\|_2 \quad \text{(Equation 3)}$$

where $M(\cdot)$ denote the binary mask of the anatomical object of interest (e.g., the prostate) and $\odot$ denotes the element-wise multiplication. A higher perceptual loss $\mathcal{L}_{percpt}$ indicates a larger observed dissimilarity in the feature space and a greater distance to the in-distribution data. The perceptual loss $\mathcal{L}_{percpt}$ is used as the uncertainty score of the input image. The uncertainty score of all 2D slices may be combined (e.g., averaged) as the score of a case.

The overall objective function for training the out-of-distribution detection framework is as follows:

$$\mathcal{L}=\lambda_1 \mathcal{L}_{compact}+\lambda_2 \mathcal{L}_{separate}+\lambda_3 \mathcal{L}_{rec}+\lambda_4 \mathcal{L}_{percpt} \quad \text{(Equation 4)}$$

The overall objective function of Equation 4 comprises the compactness loss $\mathcal{L}_{compact}$, the separateness loss $\mathcal{L}_{separate}$, a reconstruction loss $\mathcal{L}_{rec}$, and the perceptual loss $\mathcal{L}_{percpt}$ weighted by a set of hyper-parameters $\lambda 1$, $\lambda_2$, $\lambda_3$, $\lambda_4$. The reconstruction loss $\mathcal{L}_{rec}$ is defined as the L2 distance between the reconstructed image $\check{x}$ and the input image x. for penalizing the intensity differences.

$$\mathcal{L}_{rec}=\|x-\check{x}\|_2 \quad \text{(Equation 5)}$$

Once trained, the pretrained lesion detection network 206 and the trained reconstruction network 210 are applied during an online or testing stage to perform steps 108 and 110.

Embodiments described herein were experimentally validated. 2746 in-distribution cases were collected with a b-value within the range of 0 to 1200. The training and validation cases were conducted to train both the lesion detection network and the reconstruction network. For testing, there were 664 (i.e., 47% of total testing data) in-distribution cases. Additionally, 768 out-of-distribution cases (i.e., 53% of total testing data) were collected with a high b-value (larger than 1200), using different imaging protocols, and containing artifacts. Some of the out-of-distribution cases showed poor performance on lesion detection results.

Figure 3:
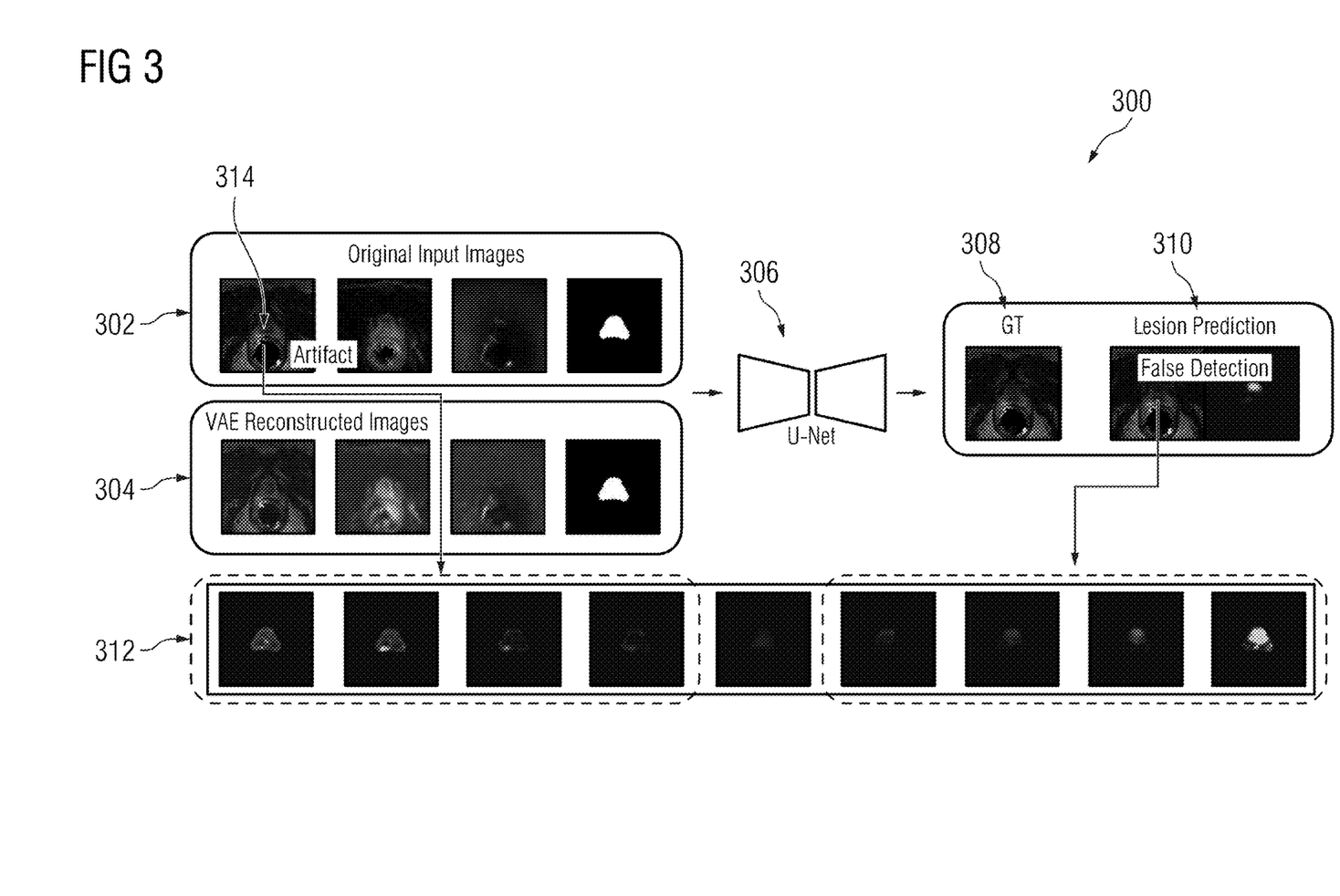
FIG. 3 shows results of a lesion detection network for an out-of-distribution case, in accordance with one or more embodiments described herein.

FIG. 3 shows results 300 of a lesion detection network for an out-of-distribution case, in accordance with one or more embodiments described herein. The lesion detection network 306 is implemented as a U-Net. Lesion detection network 306 receives input images 302 and reconstructed images 304 as input. Input images 302 show an artifact 314. Lesion detection network 306 generates lesion prediction 310, which can be compared to ground truth 308. Lesion prediction 310 is determined to be a false detection in accordance with embodiments described herein. Visualizations 312 depict pixel level uncertainty heatmaps of the average feature map difference of nine residual blocks of lesion detection network 306 within the prostate region between input images 302 and reconstructed images 304. The dissimilarity of the first four layers indicates the image level uncertainty on artifact 314. The last four layers of the decoder extract semantic relevant information for lesion prediction uncertainty. The heatmaps show the high uncertainty region for a false lesion prediction.

Figure 4:
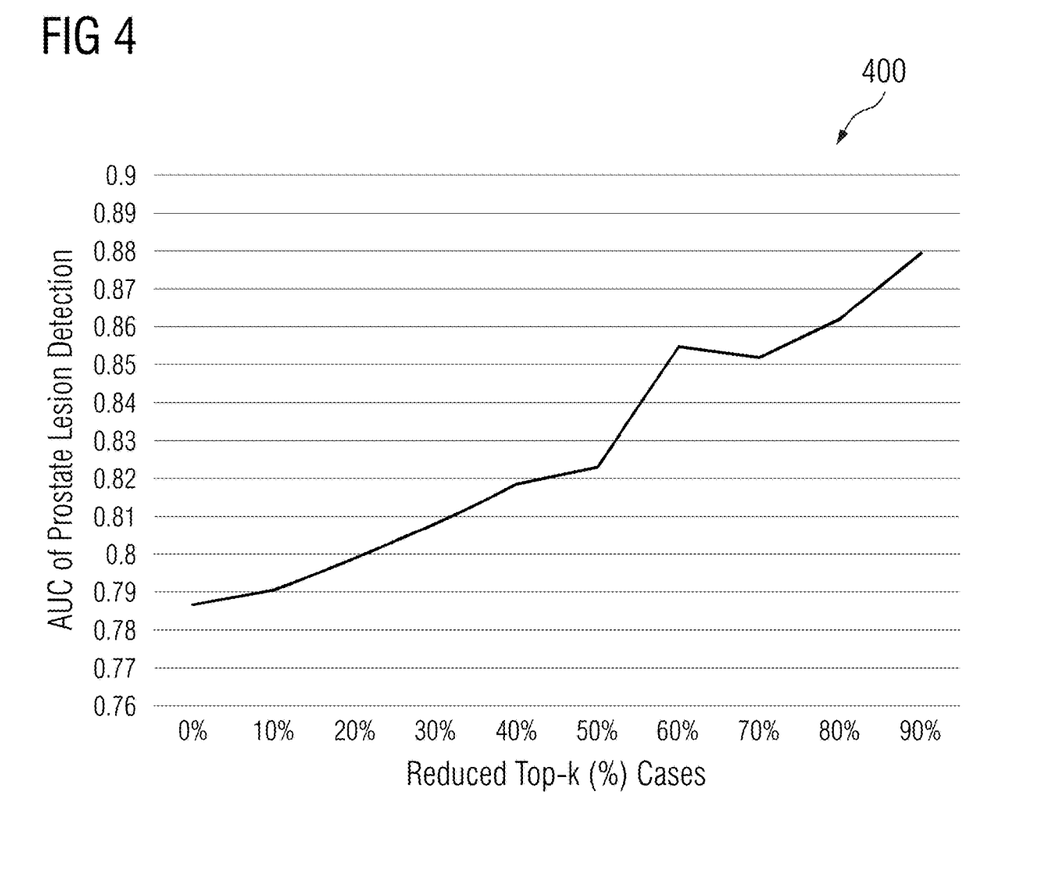
FIG. 4 shows a graph illustrating performance of one or more embodiments.

FIG. 4 shows a graph 400 illustrating performance of one or more embodiments described herein. Graph 400 shows the area under curve (AUC) for percentages of the top-k uncertainty cases rejected from the testing data. By detecting and removing the top 40% of uncertainty cases, case-level AUC is increased by 3.6% from 78.6%. As most of the out-of-distribution cases are rejected from the testing data, the performance of the lesion detection network is comparable with the AUC of 83.5% testing with the in-distribution testing data.

Embodiments described herein are described with respect to the claimed systems as well as with respect to the claimed methods. Features, advantages or alternative embodiments herein can be assigned to the other claimed objects and vice versa. In other words, claims for the systems can be improved with features described or claimed in the context of the methods. In this case, the functional features of the method are embodied by objective units of the providing system.

Furthermore, certain embodiments described herein are described with respect to methods and systems utilizing trained machine learning based networks (or models), as well as with respect to methods and systems for training machine learning based networks. Features, advantages or alternative embodiments herein can be assigned to the other claimed objects and vice versa. In other words, claims for methods and systems for training a machine learning based network can be improved with features described or claimed in context of the methods and systems for utilizing a trained machine learning based network, and vice versa.

In particular, the trained machine learning based networks applied in embodiments described herein can be adapted by the methods and systems for training the machine learning based networks. Furthermore, the input data of the trained machine learning based network can comprise advantageous features and embodiments of the training input data, and vice versa. Furthermore, the output data of the trained machine learning based network can comprise advantageous features and embodiments of the output training data, and vice versa.

In general, a trained machine learning based network mimics cognitive functions that humans associate with other human minds. In particular, by training based on training data, the trained machine learning based network is able to adapt to new circumstances and to detect and extrapolate patterns.

In general, parameters of a machine learning based network can be adapted by means of training. In particular, supervised training, semi-supervised training, unsupervised training, reinforcement learning and/or active learning can be used. Furthermore, representation learning (an alternative term is "feature learning") can be used. In particular, the parameters of the trained machine learning based network can be adapted iteratively by several steps of training.

In particular, a trained machine learning based network can comprise a neural network, a support vector machine, a decision tree, and/or a Bayesian network, and/or the trained machine learning based network can be based on k-means clustering, Q-learning, genetic algorithms, and/or association rules. In particular, a neural network can be a deep neural network, a convolutional neural network, or a convolutional deep neural network. Furthermore, a neural network can be an adversarial network, a deep adversarial network and/or a generative adversarial network.

Figure 5:
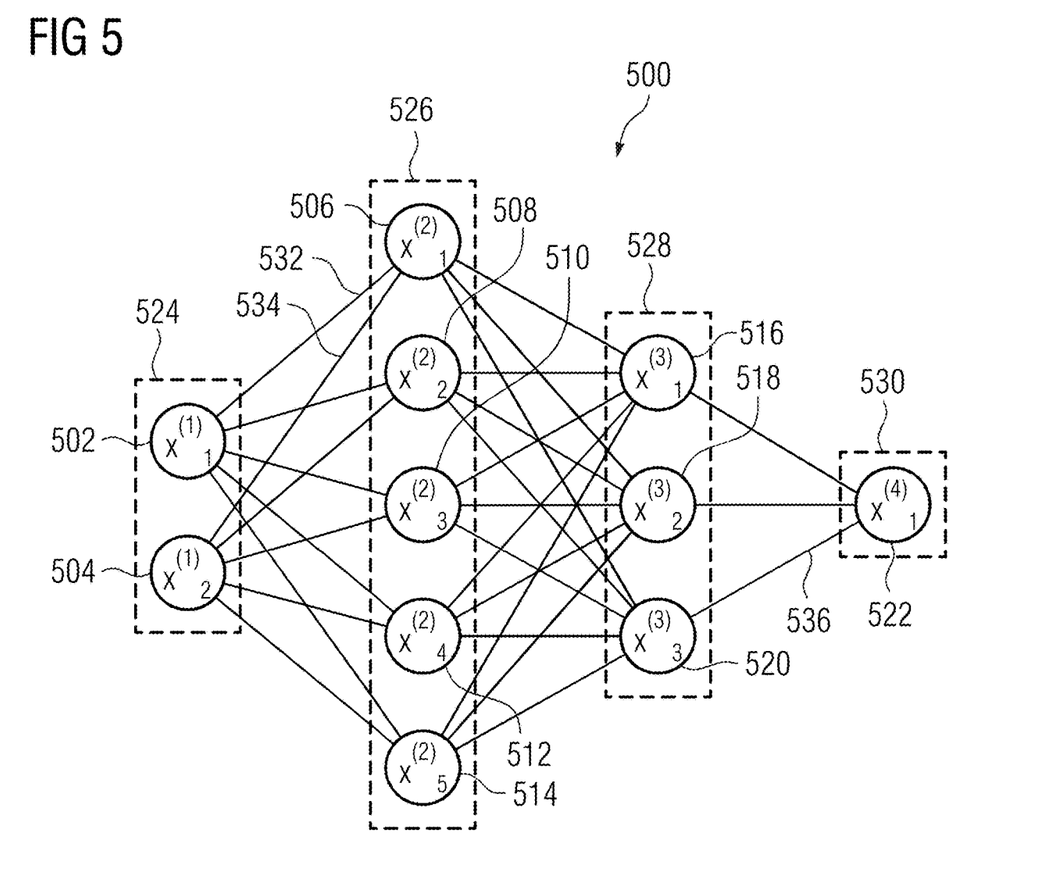
FIG. 5 shows an exemplary artificial neural network that may be used to implement one or more embodiments.

FIG. 5 shows an embodiment of an artificial neural network 500, in accordance with one or more embodiments. Alternative terms for "artificial neural network" are "neural network", "artificial neural net" or "neural net". Machine learning networks described herein, such as, e.g., the machine learning based medical imaging analysis network utilized at steps 104 and 110 and the machine learning based reconstruction network utilized at step 108 of FIG. 1 and lesion detection network 206 and reconstruction network 210 of FIG. 2, may be implemented using artificial neural network 500.

The artificial neural network 500 comprises nodes 502-522 and edges 532, 534, . . . , 536, wherein each edge 532, 534, . . . , 536 is a directed connection from a first node 502-522 to a second node 502-522. In general, the first node 502-522 and the second node 502-522 are different nodes 502-522, it is also possible that the first node 502-522 and the second node 502-522 are identical. For example, in FIG. 5, the edge 532 is a directed connection from the node 502 to the node 506, and the edge 534 is a directed connection from the node 504 to the node 506. An edge 532, 534, . . . , 536 from a first node 502-522 to a second node 502-522 is also denoted as "ingoing edge" for the second node 502-522 and as "outgoing edge" for the first node 502-522.

In this embodiment, the nodes 502-522 of the artificial neural network 500 can be arranged in layers 524-530, wherein the layers can comprise an intrinsic order introduced by the edges 532, 534, . . . , 536 between the nodes 502-522. In particular, edges 532, 534, . . . , 536 can exist only between neighboring layers of nodes. In the embodiment shown in FIG. 5, there is an input layer 524 comprising only nodes 502 and 504 without an incoming edge, an output layer 530 comprising only node 522 without outgoing edges, and hidden layers 526, 528 in-between the input layer 524 and the output layer 530. In general, the number of hidden layers 526, 528 can be chosen arbitrarily. The number of nodes 502 and 504 within the input layer 524 usually relates to the number of input values of the neural network 500, and the number of nodes 522 within the output layer 530 usually relates to the number of output values of the neural network 500.

In particular, a (real) number can be assigned as a value to every node 502-522 of the neural network 500. Here, $x^{(n)}_i$ denotes the value of the i-th node 502-522 of the n-th layer 524-530. The values of the nodes 502-522 of the input layer 524 are equivalent to the input values of the neural network 500, the value of the node 522 of the output layer 530 is equivalent to the output value of the neural network 500. Furthermore, each edge 532, 534, . . . , 536 can comprise a weight being a real number, in particular, the weight is a real number within the interval [−1, 1] or within the interval [0, 1]. Here, $w^{(m,n)}_{i,j}$ denotes the weight of the edge between the i-th node 502-522 of the m-th layer 524-530 and the j-th node 502-522 of the n-th layer 524-530. Furthermore, the abbreviation $w^{(n)}_{i,j}$ is defined for the weight $w^{(n,n+1)}_{i,j}$.

In particular, to calculate the output values of the neural network 500, the input values are propagated through the neural network. In particular, the values of the nodes 502-522 of the (n+1)-th layer 524-530 can be calculated based on the values of the nodes 502-522 of the n-th layer 524-530 by $$x_j^{(n+1)} = f(\Sigma_i x_i^{(n)} \cdot w_{i,j}^{(n)}).$$

Herein, the function f is a transfer function (another term is "activation function"). Known transfer functions are step functions, sigmoid function (e.g. the logistic function, the generalized logistic function, the hyperbolic tangent, the Arctangent function, the error function, the smoothstep function) or rectifier functions. The transfer function is mainly used for normalization purposes.

In particular, the values are propagated layer-wise through the neural network, wherein values of the input layer 524 are given by the input of the neural network 500, wherein values of the first hidden layer 526 can be calculated based on the values of the input layer 524 of the neural network, wherein values of the second hidden layer 528 can be calculated based in the values of the first hidden layer 526, etc.

In order to set the values $w^{(m,n)}_{i,j}$ for the edges, the neural network 500 has to be trained using training data. In particular, training data comprises training input data and training output data (denoted as $t_i$). For a training step, the neural network 500 is applied to the training input data to generate calculated output data. In particular, the training data and the calculated output data comprise a number of values, said number being equal with the number of nodes of the output layer.

In particular, a comparison between the calculated output data and the training data is used to recursively adapt the weights within the neural network 500 (backpropagation algorithm). In particular, the weights are changed according to $$w_{i,j}^{\prime(n)} = w_{i,j}^{(n)} - \gamma \cdot \delta_j^{(n)} \cdot x_i^{(n)}$$

wherein $\gamma$ is a learning rate, and the numbers $\delta^{(n)}_j$ can be recursively calculated as $$\delta_j^{(n)} = (\Sigma_k \delta_k^{(n+1)} \cdot w_{j,k}^{(n+1)}) \cdot f'(\Sigma_i x_i^{(n)} \cdot w_{i,j}^{(n)})$$

based on $\delta^{(n+1)}_j$, if the (n+1)-th layer is not the output layer, and $$\delta_j^{(n)} = (x_k^{(n+1)} - t_j^{(n+1)}) \cdot f'(\Sigma_i x_i^{(n)} \cdot w_{i,j}^{(n)})$$

if the (n+1)-th layer is the output layer 530, wherein f' is the first derivative of the activation function, and $y^{(n+1)}j$ is the comparison training value for the j-th node of the output layer 530.

Figure 6:
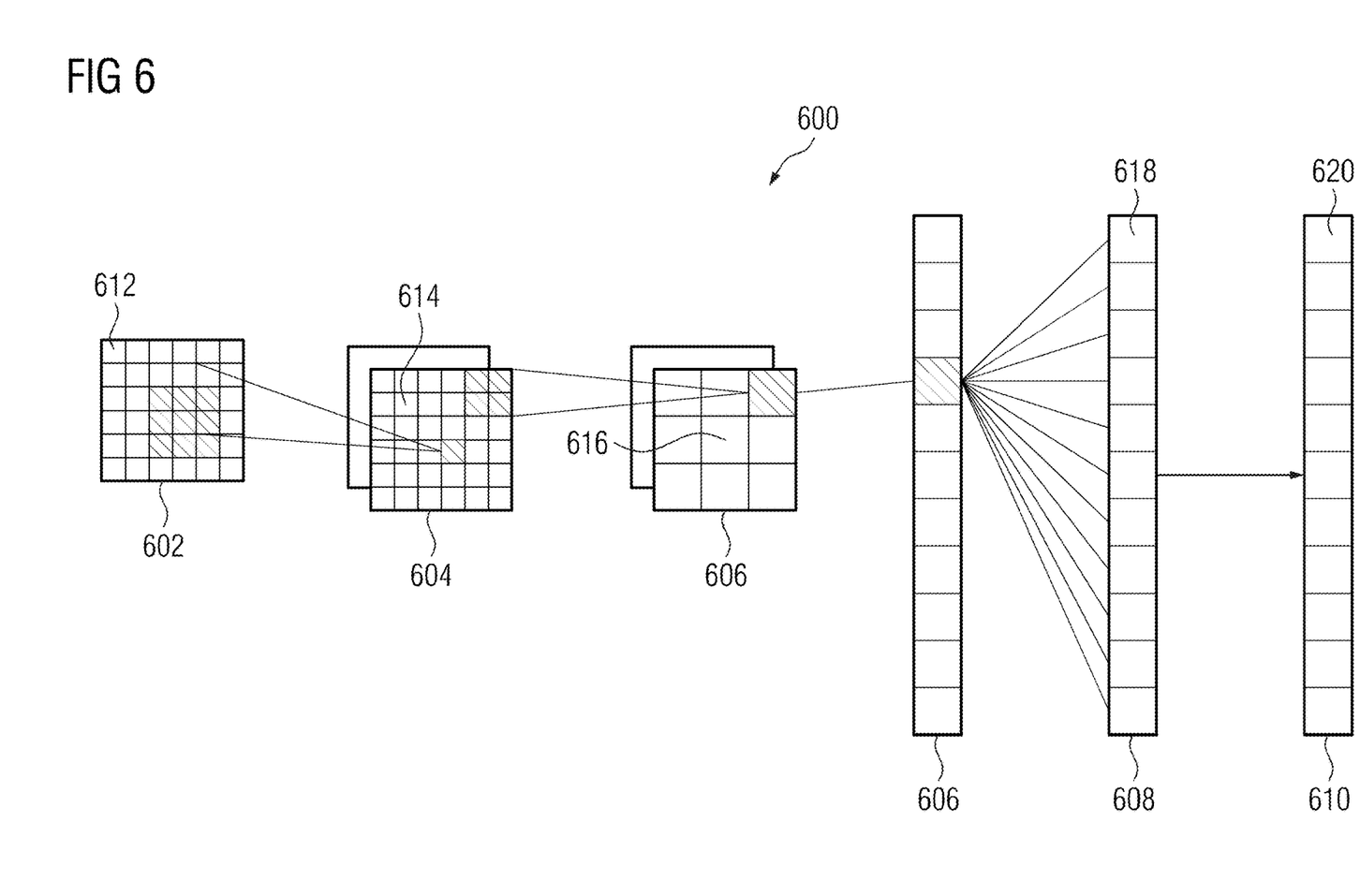
FIG. 6 shows a convolutional neural network that may be used to implement one or more embodiments.

FIG. 6 shows a convolutional neural network 600, in accordance with one or more embodiments. Machine learning networks described herein, such as, e.g., the machine learning based medical imaging analysis network utilized at steps 104 and 110 and the machine learning based reconstruction network utilized at step 108 of FIG. 1 and lesion detection network 206 and reconstruction 210 of FIG. 2, may be implemented using convolutional neural network 600.

In the embodiment shown in FIG. 6, the convolutional neural network comprises 600 an input layer 602, a convolutional layer 604, a pooling layer 606, a fully connected layer 608, and an output layer 610. Alternatively, the convolutional neural network 600 can comprise several convolutional layers 604, several pooling layers 606, and several fully connected layers 608, as well as other types of layers. The order of the layers can be chosen arbitrarily, usually fully connected layers 608 are used as the last layers before the output layer 610.

In particular, within a convolutional neural network 600, the nodes 612-620 of one layer 602-610 can be considered to be arranged as a d-dimensional matrix or as a d-dimensional image. In particular, in the two-dimensional case the value of the node 612-620 indexed with i and j in the n-th layer 602-610 can be denoted as $x^{(n)}_{[i,j]}$. However, the arrangement of the nodes 612-620 of one layer 602-610 does not have an effect on the calculations executed within the convolutional neural network 600 as such, since these are given solely by the structure and the weights of the edges.

In particular, a convolutional layer 604 is characterized by the structure and the weights of the incoming edges forming a convolution operation based on a certain number of kernels. In particular, the structure and the weights of the incoming edges are chosen such that the values $x^{(n)}_k$ of the nodes 614 of the convolutional layer 604 are calculated as a convolution $x^{(n)}_k = K_k * x^{(n-1)}$ based on the values $x^{(n-1)}$ of the nodes 612 of the preceding layer 602, where the convolution * is defined in the two-dimensional case as $$x_k^{(n)}[i,j] = (K_k * x^{(n-1)})[i,j] = \Sigma_i \Sigma_j K_k[i',j'] \cdot x^{(n-1)}[i-i',j-j'].$$

Here the k-th kernel $K_k$ is a d-dimensional matrix (in this embodiment a two-dimensional matrix), which is usually small compared to the number of nodes 612-618 (e.g. a 3×3 matrix, or a 5×5 matrix). In particular, this implies that the weights of the incoming edges are not independent, but chosen such that they produce said convolution equation. In particular, for a kernel being a 3×3 matrix, there are only 9 independent weights (each entry of the kernel matrix corresponding to one independent weight), irrespectively of the number of nodes 612-620 in the respective layer 602-610. In particular, for a convolutional layer 604, the number of nodes 614 in the convolutional layer is equivalent to the number of nodes 612 in the preceding layer 602 multiplied with the number of kernels.

If the nodes 612 of the preceding layer 602 are arranged as a d-dimensional matrix, using a plurality of kernels can be interpreted as adding a further dimension (denoted as "depth" dimension), so that the nodes 614 of the convolutional layer 604 are arranged as a (d+1)-dimensional matrix. If the nodes 612 of the preceding layer 602 are already arranged as a (d+1)-dimensional matrix comprising a depth dimension, using a plurality of kernels can be interpreted as expanding along the depth dimension, so that the nodes 614 of the convolutional layer 604 are arranged also as a (d+1)-dimensional matrix, wherein the size of the (d+1)-dimensional matrix with respect to the depth dimension is by a factor of the number of kernels larger than in the preceding layer 602.

The advantage of using convolutional layers 604 is that spatially local correlation of the input data can exploited by enforcing a local connectivity pattern between nodes of adjacent layers, in particular by each node being connected to only a small region of the nodes of the preceding layer.

In embodiment shown in FIG. 6, the input layer 602 comprises 36 nodes 612, arranged as a two-dimensional 6×6 matrix. The convolutional layer 604 comprises 72 nodes 614, arranged as two two-dimensional 6×6 matrices, each of the two matrices being the result of a convolution of the values of the input layer with a kernel. Equivalently, the nodes 614 of the convolutional layer 604 can be interpreted as arranges as a three-dimensional 6×6×2 matrix, wherein the last dimension is the depth dimension.

A pooling layer 606 can be characterized by the structure and the weights of the incoming edges and the activation function of its nodes 616 forming a pooling operation based on a non-linear pooling function f. For example, in the two dimensional case the values $x^{(n)}$ of the nodes 616 of the pooling layer 606 can be calculated based on the values $x^{(n-1)}$ of the nodes 614 of the preceding layer 604 as $$x^{(n)}[i,j] = f(x^{(n-1)}[id_1, jd_2], \ldots, x^{(n-1)}[id_1, jd_2], \ldots, x^{(n-1)}[id_1+d_1-1, jd_2+d_2-1])$$

In other words, by using a pooling layer 606, the number of nodes 614, 616 can be reduced, by replacing a number d1·d2 of neighboring nodes 614 in the preceding layer 604 with a single node 616 being calculated as a function of the values of said number of neighboring nodes in the pooling layer. In particular, the pooling function f can be the max-function, the average or the L2-Norm. In particular, for a pooling layer 606 the weights of the incoming edges are fixed and are not modified by training.

The advantage of using a pooling layer 606 is that the number of nodes 614, 616 and the number of parameters is reduced. This leads to the amount of computation in the network being reduced and to a control of overfitting.

In the embodiment shown in FIG. 6, the pooling layer 606 is a max-pooling, replacing four neighboring nodes with only one node, the value being the maximum of the values of the four neighboring nodes. The max-pooling is applied to each d-dimensional matrix of the previous layer; in this embodiment, the max-pooling is applied to each of the two two-dimensional matrices, reducing the number of nodes from 72 to 18.

A fully-connected layer 608 can be characterized by the fact that a majority, in particular, all edges between nodes 616 of the previous layer 606 and the nodes 618 of the fully-connected layer 608 are present, and wherein the weight of each of the edges can be adjusted individually.

In this embodiment, the nodes 616 of the preceding layer 606 of the fully-connected layer 608 are displayed both as two-dimensional matrices, and additionally as non-related nodes (indicated as a line of nodes, wherein the number of nodes was reduced for a better presentability). In this embodiment, the number of nodes 618 in the fully connected layer 608 is equal to the number of nodes 616 in the preceding layer 606. Alternatively, the number of nodes 616, 618 can differ.

Furthermore, in this embodiment, the values of the nodes 620 of the output layer 610 are determined by applying the Softmax function onto the values of the nodes 618 of the preceding layer 608. By applying the Softmax function, the sum the values of all nodes 620 of the output layer 610 is 1, and all values of all nodes 620 of the output layer are real numbers between 0 and 1.

A convolutional neural network 600 can also comprise a ReLU (rectified linear units) layer or activation layers with non-linear transfer functions. In particular, the number of nodes and the structure of the nodes contained in a ReLU layer is equivalent to the number of nodes and the structure of the nodes contained in the preceding layer. In particular, the value of each node in the ReLU layer is calculated by applying a rectifying function to the value of the corresponding node of the preceding layer.

The input and output of different convolutional neural network blocks can be wired using summation (residual/dense neural networks), element-wise multiplication (attention) or other differentiable operators. Therefore, the convolutional neural network architecture can be nested rather than being sequential if the whole pipeline is differentiable.

In particular, convolutional neural networks 600 can be trained based on the backpropagation algorithm. For preventing overfitting, methods of regularization can be used, e.g. dropout of nodes 612-620, stochastic pooling, use of artificial data, weight decay based on the L1 or the L2 norm, or max norm constraints. Different loss functions can be combined for training the same neural network to reflect the joint training objectives. A subset of the neural network parameters can be excluded from optimization to retain the weights pretrained on another datasets.

Systems, apparatuses, and methods described herein may be implemented using digital circuitry, or using one or more computers using well-known computer processors, memory units, storage devices, computer software, and other components. Typically, a computer includes a processor for executing instructions and one or more memories for storing instructions and data. A computer may also include, or be coupled to, one or more mass storage devices, such as one or more magnetic disks, internal hard disks and removable disks, magneto-optical disks, optical disks, etc.

Systems, apparatus, and methods described herein may be implemented using computers operating in a client-server relationship. Typically, in such a system, the client computers are located remotely from the server computer and interact via a network. The client-server relationship may be defined and controlled by computer programs running on the respective client and server computers.

Systems, apparatus, and methods described herein may be implemented within a network-based cloud computing system. In such a network-based cloud computing system, a server or another processor that is connected to a network communicates with one or more client computers via a network. A client computer may communicate with the server via a network browser application residing and operating on the client computer, for example. A client computer may store data on the server and access the data via the network. A client computer may transmit requests for data, or requests for online services, to the server via the network. The server may perform requested services and provide data to the client computer(s). The server may also transmit data adapted to cause a client computer to perform a specified function, e.g., to perform a calculation, to display specified data on a screen, etc. For example, the server may transmit a request adapted to cause a client computer to perform one or more of the steps or functions of the methods and workflows described herein, including one or more of the steps or functions of FIG. 1. Certain steps or functions of the methods and workflows described herein, including one or more of the steps or functions of FIG. 1, may be performed by a server or by another processor in a network-based cloud-computing system. Certain steps or functions of the methods and workflows described herein, including one or more of the steps of FIG. 1, may be performed by a client computer in a network-based cloud computing system. The steps or functions of the methods and workflows described herein, including one or more of the steps of FIG. 1, may be performed by a server and/or by a client computer in a network-based cloud computing system, in any combination.

Systems, apparatus, and methods described herein may be implemented using a computer program product tangibly embodied in an information carrier, e.g., in a non-transitory machine-readable storage device, for execution by a programmable processor; and the method and workflow steps described herein, including one or more of the steps or functions of FIG. 1, may be implemented using one or more computer programs that are executable by such a processor. A computer program is a set of computer program instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Figure 7:
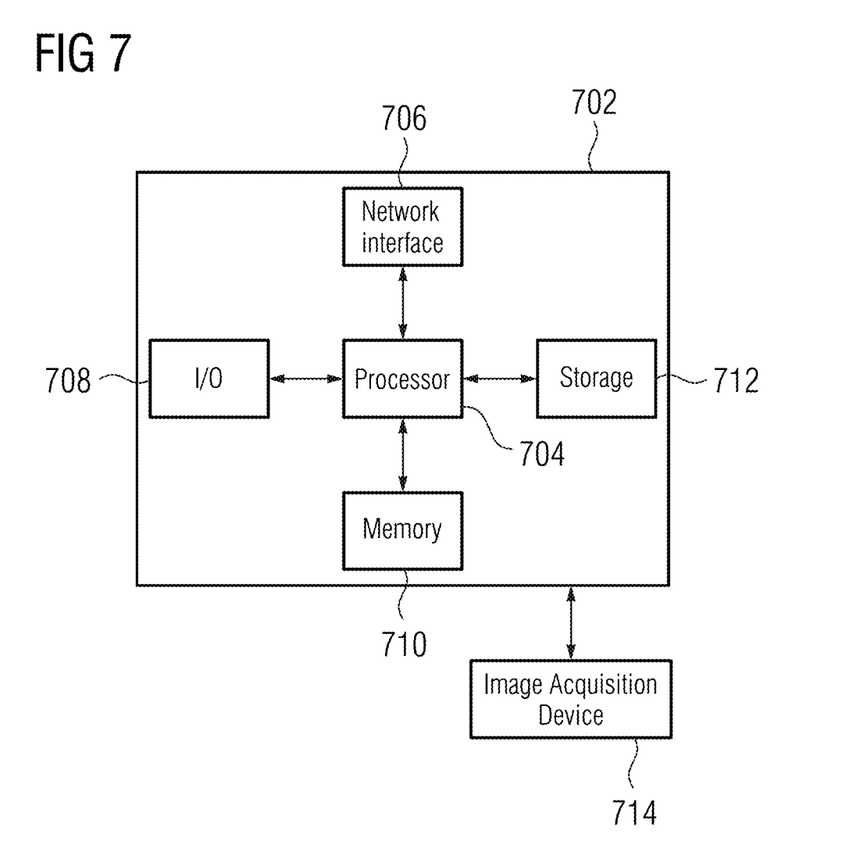
FIG. 7 shows a high-level block diagram of a computer that may be used to implement one or more embodiments.

A high-level block diagram of an example computer 702 that may be used to implement systems, apparatus, and methods described herein is depicted in FIG. 7. Computer 702 includes a processor 704 operatively coupled to a data storage device 712 and a memory 710. Processor 704 controls the overall operation of computer 702 by executing computer program instructions that define such operations. The computer program instructions may be stored in data storage device 712, or other computer readable medium, and loaded into memory 710 when execution of the computer program instructions is desired. Thus, the method and workflow steps or functions of FIG. 1 can be defined by the computer program instructions stored in memory 710 and/or data storage device 712 and controlled by processor 704 executing the computer program instructions. For example, the computer program instructions can be implemented as computer executable code programmed by one skilled in the art to perform the method and workflow steps or functions of FIG. 1. Accordingly, by executing the computer program instructions, the processor 704 executes the method and workflow steps or functions of FIG. 1. Computer 702 may also include one or more network interfaces 706 for communicating with other devices via a network. Computer 702 may also include one or more input/output devices 708 that enable user interaction with computer 702 (e.g., display, keyboard, mouse, speakers, buttons, etc.).

Processor 704 may include both general and special purpose microprocessors, and may be the sole processor or one of multiple processors of computer 702. Processor 704 may include one or more central processing units (CPUs), for example. Processor 704, data storage device 712, and/or memory 710 may include, be supplemented by, or incorporated in, one or more application-specific integrated circuits (ASICs) and/or one or more field programmable gate arrays (FPGAs).

Data storage device 712 and memory 710 each include a tangible non-transitory computer readable storage medium. Data storage device 712, and memory 710, may each include high-speed random access memory, such as dynamic random access memory (DRAM), static random access memory (SRAM), double data rate synchronous dynamic random access memory (DDR RAM), or other random access solid state memory devices, and may include non-volatile memory, such as one or more magnetic disk storage devices such as internal hard disks and removable disks, magneto-optical disk storage devices, optical disk storage devices, flash memory devices, semiconductor memory devices, such as erasable programmable read-only memory (EPROM), electrically erasable programmable read-only memory (EEPROM), compact disc read-only memory (CD-ROM), digital versatile disc read-only memory (DVD-ROM) disks, or other non-volatile solid state storage devices.

Input/output devices 708 may include peripherals, such as a printer, scanner, display screen, etc. For example, input/output devices 708 may include a display device such as a cathode ray tube (CRT) or liquid crystal display (LCD) monitor for displaying information to the user, a keyboard, and a pointing device such as a mouse or a trackball by which the user can provide input to computer 702.

An image acquisition device 714 can be connected to the computer 702 to input image data (e.g., medical images) to the computer 702. It is possible to implement the image acquisition device 714 and the computer 702 as one device. It is also possible that the image acquisition device 714 and the computer 702 communicate wirelessly through a network. In a possible embodiment, the computer 702 can be located remotely with respect to the image acquisition device 714.

Any or all of the systems and apparatus discussed herein may be implemented using one or more computers such as computer 702.

One skilled in the art will recognize that an implementation of an actual computer or computer system may have other structures and may contain other components as well, and that FIG. 7 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A computer-implemented method comprising:
receiving one or more input medical images of a patient;
generating one or more reconstructed images of the one or more input medical images using a machine learning based reconstruction network;
determining whether the one or more input medical images are out-of-distribution from training images on which a machine learning based medical imaging analysis network is trained based on the one or more input medical images and the one or more reconstructed images, wherein determining whether the one or more input medical images are out-of-distribution from training images on which a machine learning based medical imaging analysis network is trained based on the one or more input medical images and the one or more reconstructed images comprises:
extracting features from the one or more input medical images and the one or more reconstructed images using the machine learning based medical imaging analysis network; and
comparing the extracted features from the one or more input medical images and the extracted features from the one or more reconstructed images to determine whether the one or more input medical images are out-of-distribution from the training images; and
outputting the determination of whether the one or more input medical images are out-of-distribution from the training images.

2. The computer-implemented method of claim 1, wherein the machine learning based reconstruction network and the machine learning based medical imaging analysis network are trained on the same training images.

3. The computer-implemented method of claim 1, wherein comparing the extracted features from the one or more input medical images and the extracted features from the one or more reconstructed images to determine whether the one or more input medical images are out-of-distribution from the training images comprises:
calculating an uncertainty score based on a distance between the features extracted from the one or more input medical images and the features extracted from the one or more reconstructed images.

4. The computer-implemented method of claim 3, wherein comparing the extracted features from the one or more input medical images and the extracted features from the one or more reconstructed images to determine whether the one or more input medical images are out-of-distribution from the training images further comprises:
comparing the uncertainty score to a threshold.

5. The computer-implemented method of claim 1, further comprising:
performing a medical imaging analysis task from the one or more input medical images using the machine learning based medical imaging analysis network; and
outputting results of the medical imaging analysis task.

6. The computer-implemented method of claim 1, wherein the medical imaging analysis task comprises at least one of classification, detection, segmentation, quantification, or clinical decision making.

7. The computer-implemented method of claim 1, wherein the machine learning based medical imaging analysis network comprises a lesion detection network trained for detecting prostate cancer lesions in the one or more input medical images.

8. An apparatus comprising:
means for receiving one or more input medical images of a patient;
means for generating one or more reconstructed images of the one or more input medical images using a machine learning based reconstruction network;
means for determining whether the one or more input medical images are out-of-distribution from training images on which a machine learning based medical imaging analysis network is trained based on the one or more input medical images and the one or more reconstructed images, wherein the means for determining whether the one or more input medical images are out-of-distribution from training images on which a machine learning based medical imaging analysis network is trained based on the one or more input medical images and the one or more reconstructed images comprises:
means for extracting features from the one or more input medical images and the one or more reconstructed images using the machine learning based medical imaging analysis network; and
means for comparing the extracted features from the one or more input medical images and the extracted features from the one or more reconstructed images to determine whether the one or more input medical images are out-of-distribution from the training images; and means for outputting the determination of whether the one or more input medical images are out-of-distribution from the training images.

9. The apparatus of claim 8, wherein the machine learning based reconstruction network and the machine learning based medical imaging analysis network are trained on the same training images.

10. The apparatus of claim 8, wherein the means for comparing the extracted features from the one or more input medical images and the extracted features from the one or more reconstructed images to determine whether the one or more input medical images are out-of-distribution from the training images comprises:

means for calculating an uncertainty score based on a distance between the features extracted from the one or more input medical images and the features extracted from the one or more reconstructed images.

11. The apparatus of claim 10, wherein the means for comparing the extracted features from the one or more input medical images and the extracted features from the one or more reconstructed images to determine whether the one or more input medical images are out-of-distribution from the training images further comprises:

means for comparing the uncertainty score to a threshold.

12. The apparatus of claim 8, further comprising:

means for performing a medical imaging analysis task from the one or more input medical images using the machine learning based medical imaging analysis network; and means for outputting results of the medical imaging analysis task.

13. A non-transitory computer readable medium storing computer program instructions, the computer program instructions when executed by a processor cause the processor to perform operations comprising:

receiving one or more input medical images of a patient;

generating one or more reconstructed images of the one or more input medical images using a machine learning based reconstruction network;

determining whether the one or more input medical images are out-of-distribution from training images on which a machine learning based medical imaging analysis network is trained based on the one or more input medical images and the one or more reconstructed images, wherein determining whether the one or more input medical images are out-of-distribution from training images on which a machine learning based medical imaging analysis network is trained based on the one or more input medical images and the one or more reconstructed images comprises:

extracting features from the one or more input medical images and the one or more reconstructed images using the machine learning based medical imaging analysis network; and comparing the extracted features from the one or more input medical images and the extracted features from the one or more reconstructed images to determine whether the one or more input medical images are out-of-distribution from the training images; and outputting the determination of whether the one or more input medical images are out-of-distribution from the training images.

14. The non-transitory computer readable medium of claim 13, wherein the machine learning based reconstruction network and the machine learning based medical imaging analysis network are trained on the same training images.

15. The non-transitory computer readable medium of claim 13, wherein comparing the extracted features from the one or more input medical images and the extracted features from the one or more reconstructed images to determine whether the one or more input medical images are out-of-distribution from the training images comprises:

calculating an uncertainty score based on a distance between the features extracted from the one or more input medical images and the features extracted from the one or more reconstructed images.

16. The non-transitory computer readable medium of claim 13, wherein the medical imaging analysis task comprises at least one of classification, detection, segmentation, quantification, or clinical decision making.

17. The non-transitory computer readable medium of claim 13, wherein the machine learning based medical imaging analysis network comprises a lesion detection network trained for detecting prostate cancer lesions in the one or more input medical images.

* * * * *